(12) United States Patent
Ma

(10) Patent No.: US 6,875,605 B1
(45) Date of Patent: Apr. 5, 2005

(54) MODULAR CELL CULTURE BIOREACTOR AND ASSOCIATED METHODS

(75) Inventor: Teng Ma, Tallahassee, FL (US)

(73) Assignee: Florida State University Research Foundation, Inc., Tallahassee, FL (US)

(*) Notice: Subject to any disclaimer, the term of this patent is extended or adjusted under 35 U.S.C. 154(b) by 0 days.

(21) Appl. No.: 10/645,350

(22) Filed: Aug. 21, 2003

Related U.S. Application Data

(60) Provisional application No. 60/405,040, filed on Aug. 21, 2002, and provisional application No. 60/405,041, filed on Aug. 21, 2002.

(51) Int. Cl.$^7$ .................................................. C12N 5/02
(52) U.S. Cl. ..................................... 435/297.1; 435/399
(58) Field of Search ............................... 435/297.1, 399

(56) References Cited

PUBLICATIONS

Pazzano et al.; "Comparison of Chondrogenis in Static and Perfused Bioreactor Culture;" Biotechnol. Prog vol. 16; No. 5; pp. 893–896; 2000.
Ingram et al.; "Three–Dimensional Growth Patterns of Various Human Tumor Cell Lines in Simulated Microgravity of A NASA Bioreactor," In Vitro Cell. Dev. Biol.—Annual; pp. 459–466; Jun. 1997.
Bannu et al.; "Cytokine–Augumented Culture of Haematopoietic Progenitor Cells in a Novel Three–Dimensional Cell Growth Matrix;" Cytokine; vol. 13, No. 6; Mar. 21, 2000; pp. 349–358.
Bagley et al.; "Extended culture of miltipotent hematopoietic progenitors without cytokine augmentation in a novel three–dimensional device," Experimental Hematoloty 27 (1999); pp. 496–504.
Obradovic et al.; "Gas Exchange is Essential for Bioreactor Cultivation of Tissue Engineered Cartilage," Biotechnology and Bioengineering; vol. 63, No. 2, Apr. 20, 1999; pp. 197–205.
Hoerstrup, MD et al.; "New Pulsatile Bioreactor for In Vitro Formation of Tissue Engineered Heart Valves;" Tissue Engineering; vol. 6, No. 1, 2000; pp. 75–78.
Halberstadt et al.; "The In Vitro Growth of a Three–Dimensional Human Dermal Replacement Using a Single–Pass Perfusion System;" Biotechnology and Bioengineering; vol. 43, No. 4, 1994; pp. 740–746.
Vunjak–Nokakovic et al.; "Dynamic Cell Seeding of Polymer Scaffolds for Cartilage Tissue Engineering;" Biotechnol. Prog. 1998, vol. 14, No. 2; pp. 193–202.

Kim, MD et al.; "Dynamic Seeding and in Vitro Culture of Hepatocytes in a Flow Perfusion System;" Tissue Engineering; vol. 6, No. 1, 2000; pp. 39–44.
Ma et al.; "Development of an In Vitro Human Placenta Model by the Cuotivation of Human Trophoblasts in a Fiber–Based Bioreactor System;" Tissue Engineering; vol. 5, No. 2; (1999); pp. 91–101.
Freed et al.; "Cuotivation of Cell–Polymer Cartilage Implants in Bioreactors;" Journal of Cellular Biochemistry vol. 51; 1993; pp. 257–264.
Sittinger; "Artificial tissues in perfusion culture;" The International Journal of Artificial Organs; vol. 20, No. 1; 1997; pp. 57–62.
Niklason; "Functional Arteries Grown in Vitro;" Science; vol. 284; Apr. 16, 1999; pp. 489–493.
Nielsen; "Bioreactors For Hematopoietic Cell Culture;" Annu. Rev. Biomed. Eng.; 1999; pp. 129–152.
Li et al.; "Human Cord Cell Hematopoiesis in Three Dimensional Nonwoven Firbous Matrices: In Vitro Simulation of the Marrow Microenvironment"; Journal of Hematotherapy & Stem Cell Research; vol. 10; 2001; pp. 355–368.
Collins et al.; "Characterization of Hematopoietic Cell Expansion, Oxygen Uptake, and Glycolysis in a Controlled, Stirred–Tank Bioreactor System;" Biotechnol. Prog. 1998 vol. 14; pp. 466–472.
Ma et al.; Oxygen Tension Influences Proliferation and Differentialtion in a Tissue–Engineered Model of Placental Trophoblast–Like Cells; Tissue Engineering, vol. 7, No. 5, 2001; pp. 495–506.

*Primary Examiner*—James Ketter
(74) *Attorney, Agent, or Firm*—Allen, Dyer, Doppelt, Milbrath & Gilchrist , P.A.

(57) ABSTRACT

An apparatus and method for a modular cell culture bioreactor comprises a plurality of chambers for cell culture; at least one reservoir containing a cell support medium; a plurality of conduits fluidly connecting the at least one reservoir with the plurality of chambers; and at least one pump fluidly connected through the plurality of conduits with the at least one reservoir and with the plurality of chambers to pump cell support medium therethrough; wherein each individual chamber of the plurality of chambers includes at least one three-dimensional matrix comprising polyethylene terephthalate, a plurality of channels carrying the cell support medium and having the matrix positioned in fluid communication therebetween, and at least two openings into each the channel, wherein a first the opening is in fluid connection with the pump and a second the opening is in fluid connection with the reservoir.

16 Claims, 14 Drawing Sheets

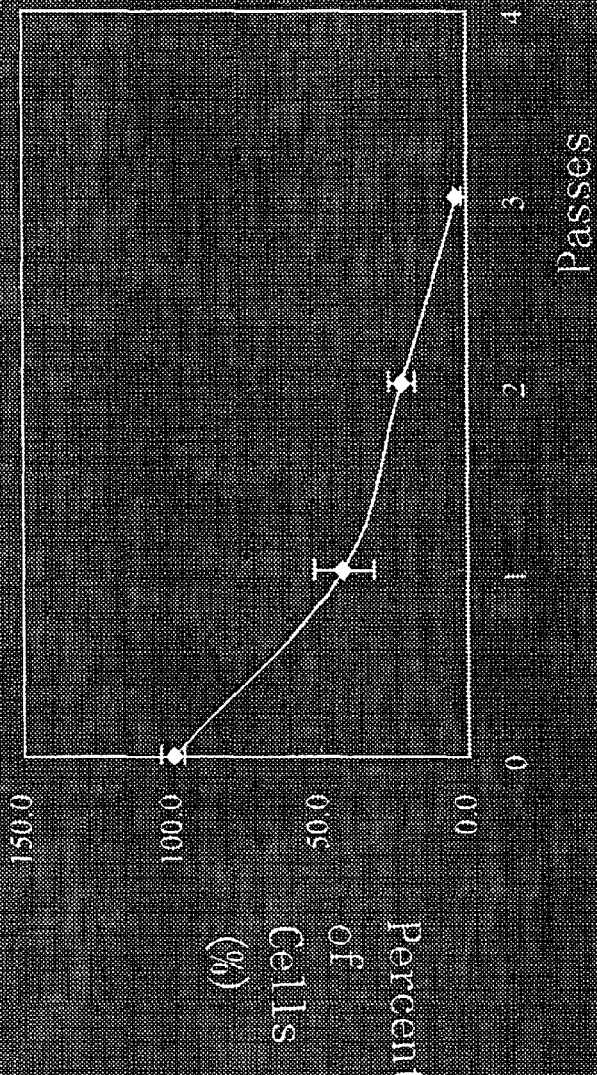

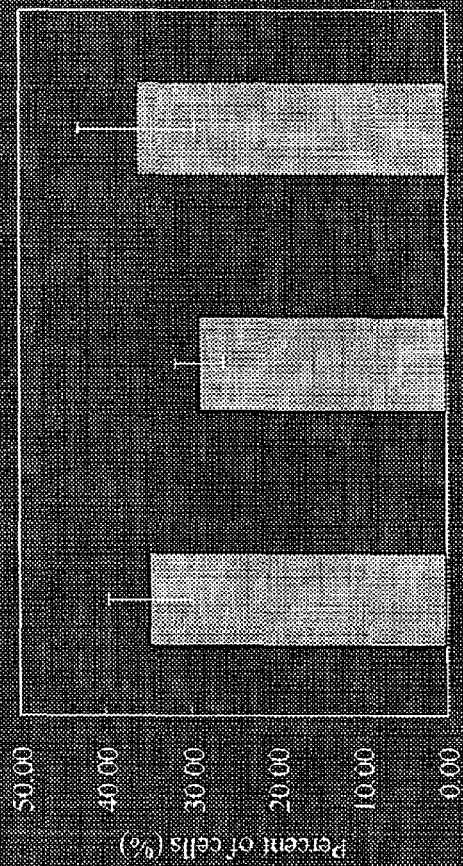

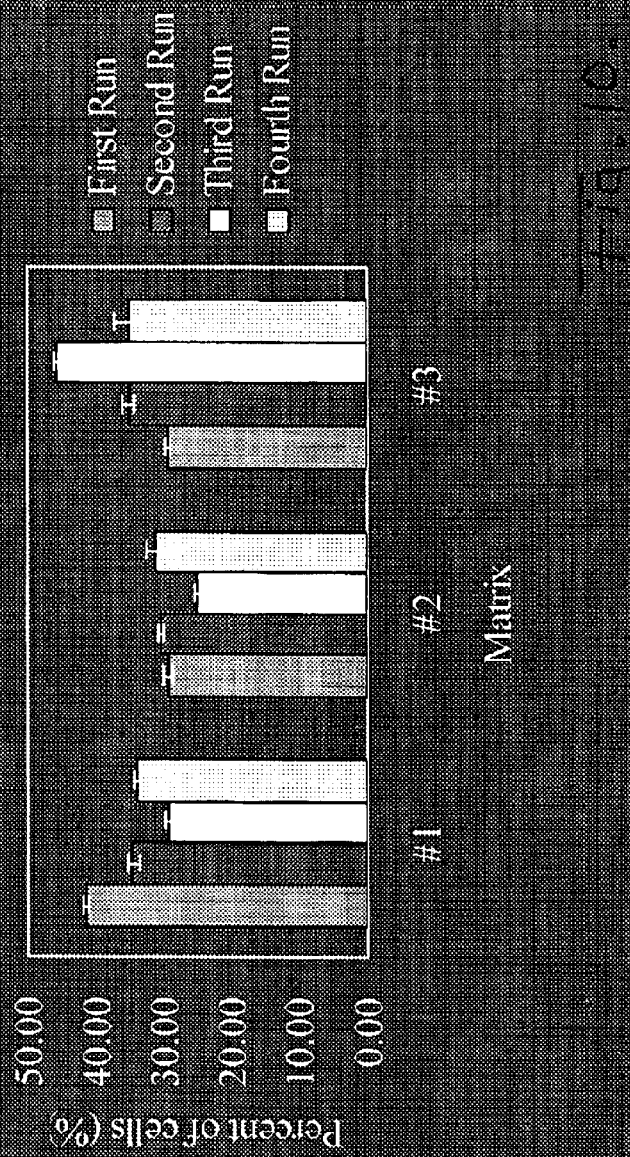

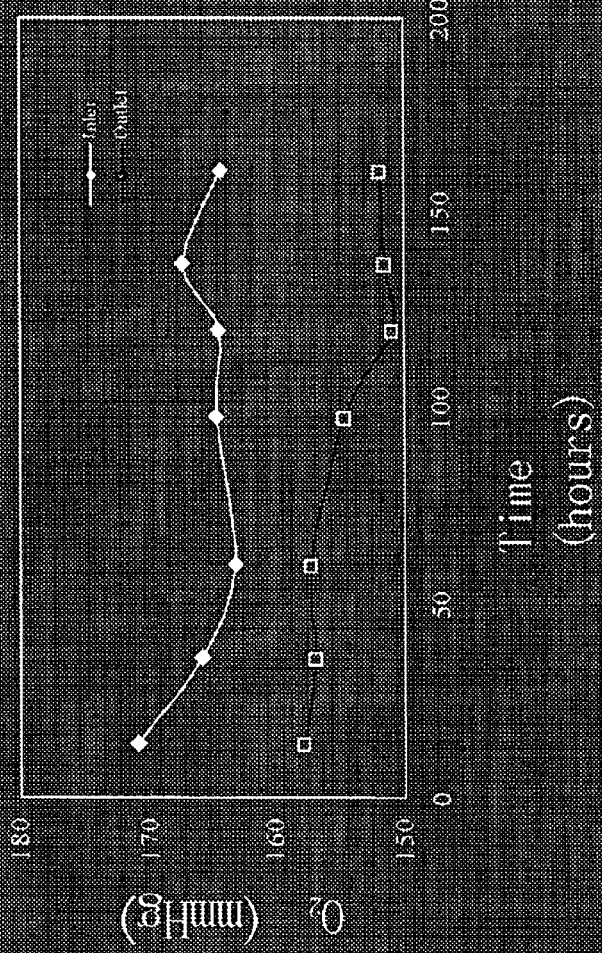

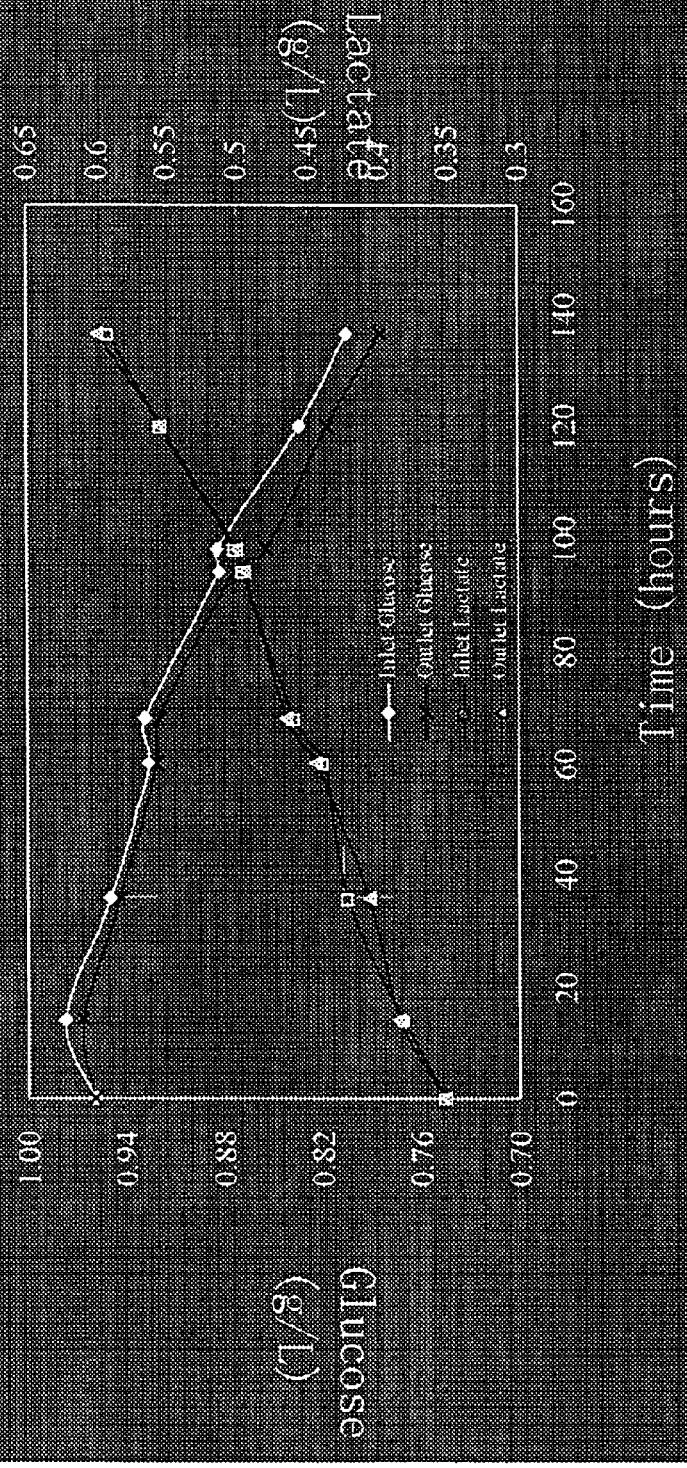

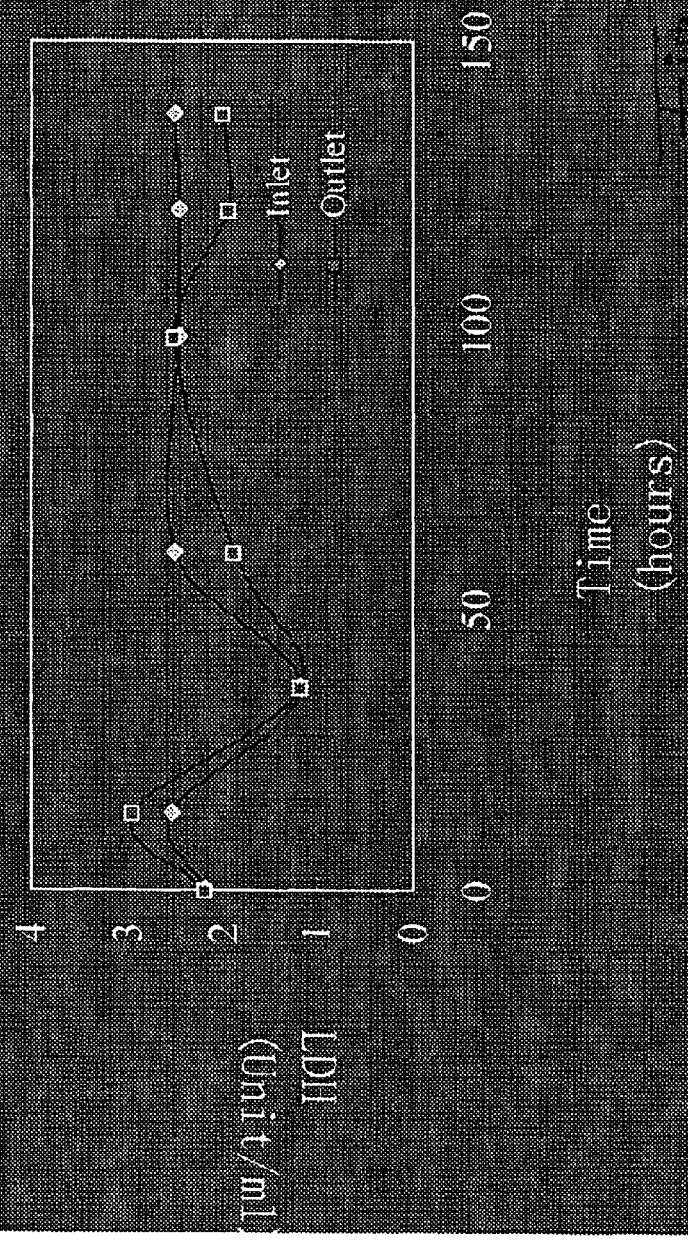

MODULAR CELL CULTURE BIOREACTOR AND ASSOCIATED METHODS

RELATED APPLICATION

This application claims priority from co-pending provisional applications Ser. Nos. 60/405,040 and 60/405,041, which were filed on Aug. 21, 2002, and which are incorporated herein by reference in their entirety.

FIELD OF THE INVENTION

The present invention relates to the field of tissue engineering and, more particularly, to a modular bioreactor system which integrates cell seeding and cell culture, and associated methods.

BACKGROUND OF THE INVENTION

Engineered tissues, especially human tissues, offer great hope for treatment of a variety of diseases and for repair of damage to natural tissues due to trauma. Adults produce about 400 billion cycling cells daily, and loss of production of these cells is life threatening. In treating cancer patients, chemotherapy and radiation are commonly used; however, high-dose toxic drugs and irradiation not only kill cancer cells but also healthy hematopoietic cells produced by human bone marrow. Red blood cell and platelet transfusion and hematopoietic stem cell and progenitor cell (HSC/HPC) infusion are two commonly used clinical methods to replace mature blood cells and to reconstitute the blood-producing capacity of the patient. However, allogeneic matched donors are difficult to find and autologous HSC/HPC may be contraindicated or limited. Cord blood (CB) cells are obtained from umbilical cord of newborn babies and are rich in CD34+ cells and easy to procure. The challenge is to expand CB cells to large enough quantities for adult patients or for repeated transplant. Attempted improvements to ex vivo expansion methodologies have included the use of exogenous cytokines or growth factors or altering culture parameters such as culture duration and feeding schedules, which influence the differentiation and self-renewal of HSC/HPC. The ideas of these studies were to mimic the key elements of in vivo hematopoiesis environment, including soluble factors (e.g., cytokines), support cells and adhesion molecules, and physiochemical parameters.

However, to date, the field of hematotherapy has not extensively examined the effects of three-dimensional (3-D) geometry of the in vivo HSC/HPC environment and has failed to replicate the 3-D geometry in the ex vivo expansion systems. It is well established that cellular activities, including migration, proliferation, differentiation, and tissue functions, are significantly affected by cellular organization and structural cues both in vivo and in ex vivo cultures. Based on this knowledge, we have developed a 3-D small-scale culture system for ex vivo growth of HSC/HPC using a polyethylene terephthalate (PET) non-woven matrix. Our preliminary data show a substantial advantage for growth of CD34+ positive cells and committed colony forming units (CFU) in this 3-D matrix compared to standard two-dimensional control cultures. To successfully apply the 3-D culture system for clinical use, a perfusion bioreactor system is critically needed. The perfusion bioreactor system provides an environment for continuous nutrient delivery and waste removal, and thus sustains a high cell density in a 3-D matrix over an extended culture period. In addition, the perfusion bioreactor system can be automatically controlled and is less demanding for operation and culture handling, an important requirement for clinical use.

Also of interest are the cells in human bone marrow, as bone marrow contains hematopoietic tissue and the associated supporting stroma. While the hematopoietic stem cells produce mature blood cells, marrow stromal or stem cells (MSC) are the progenitor cells of skeletal tissue components and have the ability to differentiate into cell types phenotypically unrelated such as osteocytes, chondrocytes, muscle cells, adipocytes, and cardiomyocytes. Propelled by an increasing knowledge of human mesenchymal stromal cells (hMSC) biology, clinical evidence is emerging in the literature suggesting the tantalizing potential of hMSC for treating a wide range of diseases including osteogenesis imperfecta, tendon repair, stroke, and heart failure (8–11). For example, hMSC can be converted into myogenic progenitors in response to physiological stimuli, thus providing an alternative strategy for treatment of muscle dystrophies (3). In a recent study, researchers showed that injected bone marrow cells can form myocardial tissue and partially restored lost heart function in mice (24). To utilize hMSCs in clinical practice, a major obstacle, however, is to expand them to large quantity and yet retain their differentiation potential during the expansion.

The multi-potential properties of hMSC were first observed in the mid-1970s when whole bone marrow was grown in plastic culture dishes (18; 19). A small fraction of cells can be easily isolated by their adherence to the plastic surface after non-adherent blood cells were poured off. These adherent cells exhibited heterogeneous appearance and possessed striking features of self-renewal and differentiation even after 20 to 30 cell doublings (20). Recently, a more homogeneous (98% at passage 2) population of human MSC was obtained from bone marrow by using a density gradient to eliminate unwanted cell types (2). The cell population was expanded extensively on plastic culture dish and it maintained the ability to differentiate into multiple cell types in vitro, including adipogenic, chondrogenic, and osteogenic lineages (2). In a detailed study on purified hMSC growth kinetics, selfrenewal, and the osteogenic differentiation, hMSC was expanded for over $1.2 \times 10^9$ folds for 10 passages and maintained osteogenic differentiation capacity (4). However, a gradual increasing replicative senescence determined by the loss of population doubling potential after the first passage was observed. A recent study also reported a diminishing proliferation rate and a gradual loss of hMSC's differentiation capacity. The average doubling time increased from 1.3 for fresh bone marrow to 7.7 at passage 1 and up to 15.8 at passage 5, whereas adipogenesis started fading by 18 doublings and is totally lost by 22 passages (13). Studies have found that seeding density has profound effects on the growth rate of plastic-adherent cells from human bone marrow (12; 23). When the purified hMSCs were plated at low densities of 1.5 to 3.0 cells/cm2, they generated single-cell derived colonies and amplified about 109-fold in 6 wk (12). These single-cell-derived colonies contained three morphologically distinct cell types: spindle-shaped cells, large flat cells, and very small round cells, suggesting a heterogeneous cell population (12; 23). Compared to large cells, small round cells have greater rate of replication and enhanced potential for multi-lineage differentiation (23). The heterogeneous cell population and sensitivity to plating density were also observed for rat marrow stromal cells (14). Cell growth sensitivity to plating density may be explained by cell—cell contact and low seeding density appears to greatly enhance hMSC self-renewal and retain differentiation potential.

However, prior protocols used in obtaining and expanding hMSC require frequent cell passages and very large surface area for cells to grow. They are not designed for ex vivo expanding a large quantity of hMSC for clinical use. The 3-D feature, which is characteristic for hMSC in vivo environment, is also missing in the preparation. Many clinical cases require the reconstruction of a functional tissue in vitro before being transplanted to replace the damaged one. This becomes especially critical when the defect is larger than those that would spontaneously heal such as a large area of skin and a large bone defect, or when the immediumte replacement of tissue function is needed such as the replacement of cardiac muscle function. In these cases, a large number of cells alone are not sufficient; the cell must also exhibit desired functions or can be induced into a functional state once placed in the injury site. To achieve this, 3-D culture systems offer many advantages over conventional 2-D culture systems. A 3-D matrix offers a high surface area per unit volume and captures the 3-D feature of the in vivo tissue. Matrices that offer a 3-D structure have been widely used for tissue engineering a wide variety of tissues and for ex vivo expanding human hematopoietic progenitors (25–36). Among the materials used in these studies, non-woven fibrous matrix offers unique advantages. The non-woven fibrous matrix has isotropic structure, e.g., it has the same properties at three coordinates. In these matrices, regardless of where a cell lands, there will be the same amount of surface area available to it and it would have the same opportunity to interact with other cells. It also provides an environment where cells will have intimate interactions with neighboring cells and ECM network, which is a defining feature of in vivo tissue.

Three-dimensional matrices such as collagen gels, porous gelatin sponges, porous hydroxyapatite ceramic carrier, and a composite of hydroxyaptite/tricalcium phosphate (HA/TCP) particles have been previously investigated for cartilage and bone regeneration from hMSC (37–40). Particle size and shape, seeding density, and contraction kinetics influenced the growth and secretion of ECM proteins by hMSC. In these studies, hMSCs were first expanded in culture and then loaded onto the matrices. The end results were evaluated based on the performance after implantation. Despite the successes, a number of questions remain to be answered. The ex vivo expansion of hMSC is not carried out on these matrices. It also lacks the detailed information on how hMSCs adhere to the surfaces of the scaffolds and how the structures of the scaffolds affect their proliferation. A single device combining hMSC isolation, adhesion, expansion, and modularity will be of great advantage in simplifying the operation, especially in clinical use. In addition, hMSC grown at high density in a 3-D matrix may be directly induced to differentiate into desired functional tissues and be used in repairing large wounds. The critical requirements for the 3-D expansion system are high yield for hMSC isolation, high expansion rate, maintenance of primitiveness, and formation of desired tissue structure. For clinical use, the system should meet these requirements in one single unit.

SUMMARY OF THE INVENTION

With the foregoing in mind, the present invention advantageously provides a modular cell culture bioreactor apparatus for ex vivo expansion of HSC/HPC from cord blood and bone marrow samples. A three-dimensional (3-D) perfusion bioreactor system having a plurality of cell culture chambers comrprising nonwoven PET matrices is described for ex vivo HSC/HPC expansion. Operational parameters of the 3-D perfusion bioreactor system for dynamic cell seeding and harvesting have been determined. Preferred conditions are indicated for operation of the apparatus for ex vivo HSC/HPC expansion.

Accordingly, the invention includes a modular cell culture bioreactor apparatus. The apparatus comprises a plurality of chambers for cell culture; at least one reservoir containing a cell support medium; a plurality of conduits fluidly connecting the at least one reservoir with the plurality of chambers; and at least one pump fluidly connected through the plurality of conduits with the at least one reservoir and with the plurality of chambers to pump cell support medium therethrough. Each individual chamber of the plurality of chambers includes at least one three-dimensional matrix comprising polyethylene terephthalate, a plurality of channels carrying the cell support medium and having the matrix positioned in fluid communication therebetween, and at least two openings into each the channel, wherein a first the opening is in fluid connection with the pump and a second the opening is in fluid connection with the reservoir. The bioreactor apparatus is termed modular since the cell culture chambers are connected therein in parallel and each individual cell culture chamber may be independently disconnected from the apparatus while the apparatus continues to run with the remaining chambers in place.

In a preferred apparatus, the bioreactor matrix further comprises a nonwoven fibrous matrix of polyethylene terephthalate having a random microscopic structure. The matrix may have a thickness ranging from approximately 0.5 mm to 2.0 mm, and a a void to total volume ratio greater than approximately 0.8.

In use, the bioreactor apparatus includes cell support medium having an oxygen tension ranging approximately from 1% up to 20%. At least one pump generates a cell support medium flow rate of at least approximately 0.4 ml per minute through the bioreactor, the cell medium having a pH ranging approximately from 7.0 to 7.4.

Additionally, each individual chamber of the plurality of chambers comprises a valve positioned to control fluid flow through each the opening into each channel. More specifically, each individual chamber of the plurality of chambers comprises a valve positioned to shut off fluid flow to each the opening into each channel so as to permit each individual chamber to be disconnected and removed from the bioreactor apparatus. It should also be understood that the bioreactor apparatus further comprises means for maintaining a temperature effective for cell culture. The temperature maintaining means includes an incubator in which the entire apparatus is situated, or a temperature-controlled room, for example. Also, to maintain proper incubation temperature, each individual chamber of the plurality of chambers further comprises a water jacket along an outer periphery of the chamber, the water jacket in fluid connection with a water reservoir having a heater associated therewith for maintaining the water at a temperature effective for cell culture. In the apparatus, each individual chamber of the plurality of chambers may also further comprise a jacket along an outer periphery of the chamber, the jacket circulating a heat transfer fluid around the chamber.

A method aspect of the invention includesfiltering a medium carrying an inoculum containing cells through a three-dimensional matrix containing polyethylene terephthalate, wherein filtering is accomplished at a flow rate effective for permitting adherence to the matrix by predetermined cells; and diverting the course of the flow after filtering so that the medium flows essentially along peripheries of the three-dimensional matrix. In the method, the inoculum may consist of a sample of human bone marrow, or may contain human mesenchymal stromal cells, or human hematopoietic stem cells. In the method filtering and diverting are carried out within a single cell culture chamber, may be carried out substantially simultaneously in a plurality of cell culture chambers, and may be carried out without handling the matrix.

The method may additionally comprise monitoring cell count in the filtered medium as an indicator of cell adherence to the matrix and continuing filtration until a predetermined proportion of cells has adhered, and diverting the course of the flow after filtering so that the medium flows essentially along peripheries of the three-dimensional matrix.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which:

FIG. 8 shows a graph illustrating removal of seeded cells by the bioreactor matrix during consecutive passes through the matrix;

FIG. 9 is a bar graph showing the distribution of cells seeded into a bioreactor chamber in the apparatus of FIG. 6, wherein each bioreactor has three matrices, as shown;

FIG. 10 shows a bar graph depicting distribution of seeded cells onto matrices 1, 2 and 3 during four consecutive passes of a seed cell inoculum in the apparatus of FIG. 6;

FIG. 11 is a line graph showing typical oxygen consumption of human mesenchymal stromal cells in a bioreactor at ambient $O_2$ tension;

FIG. 12 is a line graph showing glucose and lactate levels at bioreactor chamber inlet and outlet as measures of cell metabolism in the apparatus of FIG. 6; and FIG. 13 shows bioreactor chamber inlet and outlet levels of lactic acid dehydrogenase (LDH) during cell culture in the apparatus of FIG. 6.

DETAILED DESCRIPTION OF THE PREFERRED EMBODIMENT

Figure 1A:
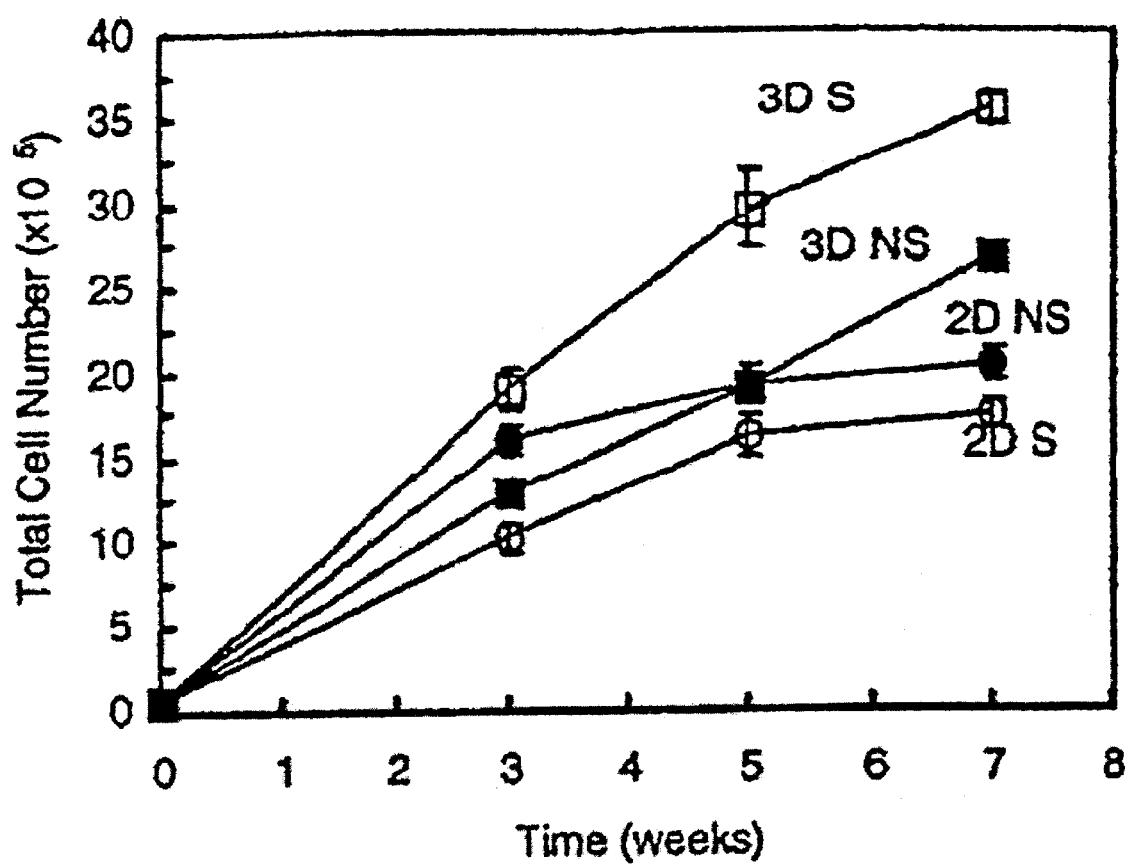
FIGS. 1(A) and (B) show culture output in two-dimensional and three-dimensional cord blood cultures in presense or absence of serum.

The present invention will now be described more fully hereinafter with reference to the accompanying drawings, in which preferred embodiments of the invention are shown. Unless otherwise defined, technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including any definitions, will control. In addition, the materials, methods and examples given are illustrative in nature only and not intended to be limiting. Accordingly, this invention may, however, be embodied in many different forms and should not be construed as limited to the illustrated embodiments set forth herein. Rather, these illustrated embodiments are provided solely for exemplary purposes so that this disclosure will be thorough and complete, and will fully convey the scope of the invention to those skilled in the art. Other features and advantages of the invention will be apparent from the following detailed description, and from the claims.

Ex Vivo Expansion of Human Hematopoietic Cells from Cord Blood.

A non-woven matrix of polyethylene terephthalate (PET) for tissue engineering differs from other porous medium in that a fibrous PET matrix has a high porosity (void to total volume ratio), usually larger than 85%, and high surface area per unit volume. These structural features provide a matrix having a large surface area for cell adherence and yet porous enough to facilitate nutrient transport to the cells grown in the matrix. PET, also known as Dacron, has been approved for medical use and has been commonly used in vascular surgery. It shows good biocompatability when used in culturing hematopoietic cells. PET matrices for use herein were prepared according to our previously developed thermal compression technique and modification of the spatial structure, e.g., porosity and pore size, of the non-woven matrices (Li Y, Ma T, Yang ST, Kniss DA. Modification and characterization of PET non-woven fibrous matrix as cell culture scaffold. Biomaterials 2001; 22:609–18). We have also quantified the matrix structure using a liquid extrusion method, as known in the art, which gives precise information on the effective pore radius and pore size distribution in the matrix. Using these techniques, PET fibrous matrices have been formed having porosities of 0.849, 0.895, and 0.926. The thickness of these matrices is also controlled, ranging from 0.5 mm to 2.0 mm.

It is known that there is a close correlation between the matrix structure and tissue development pattern. Using a dual-wave length staining technique and confocal microscopy, we have been able to quantify the 3-D structure of cell growth and to localize the cells at different cell cycle stages. Utilizing different cellular markers, we have analyzed the cell micro environment and established the correlation between the spatial position of an individual cell and its cell cycle phase. Using these techniques, we have been able to improve the structure of the 3-D scaffold according to the specific needs of a culture system. The hematopoietic microenvironment composed of nonwoven matrix and human cord blood (CB) cells is thought to mimic the marrow microenvironment and to help expand cord hematopoietic stem cells and prgenitor cells (HSC/HPC). The nonwoven PET fabric used herein has a relatively defined microstructure as the 3-D scaffold and was treated by hydrolysis so that its surface improved in cell adhesion. Different cell organizations formed in 3-D matrix in a developmental manner, from individual cells and cells bridging between fibers to large cell aggregates. Both stromal and hematopoietic cells were spatially distributed within the scaffold. Culture in this 3-D nonwoven matrix enhanced intimate cell—cell and cell-matrix interactions and allowed 3-D distribution of stromal and hematopoietic cells.

Figure 1B:
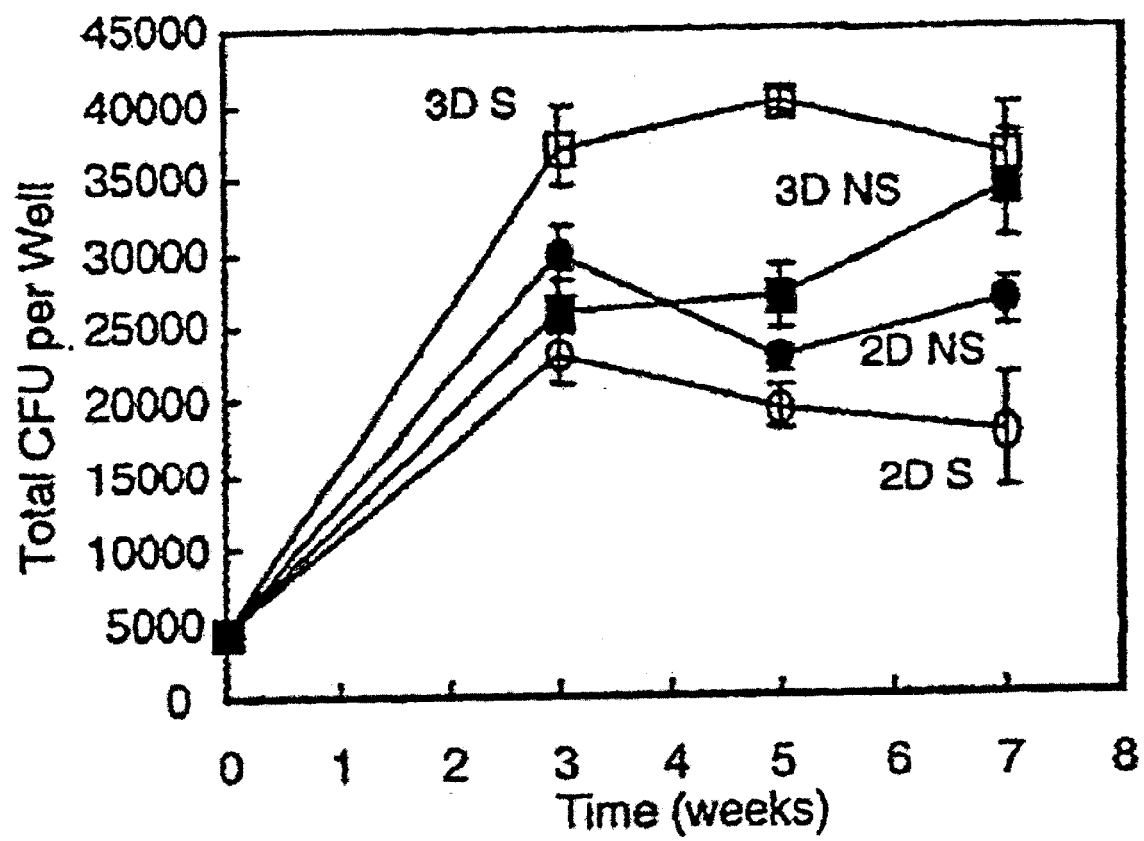

The formation of cell aggregates and higher progenitor content indicated that the spatial microenvironment in the 3-D culture played an important role in promoting hematopoiesis. Compared to two-dimensional CD34+ cell culture, 3-D culture produced 30–100% higher total cells and progenitors without added cytokines in a serum-containing system (FIG. 1). With thrombopoietin and fit-3/flk-2 ligand, it supported 2–3 fold higher total cell number (62.1 vs. 24.6 fold), CD34+ cell number (6.8 vs. 2.8 fold) and CFU number for 7–9 weeks (N=6), indicating a hematopoiesis pathway that promoted progenitor production (FIG. 1). These early static culture studies suggest that 3-D culture system can be used as an in vitro model to study stem cell or progenitor behavior, and to achieve sustained HSC/HPC expansion.

Perfusion Bioreactor Apparatus for Tissue Engineering

The bioreactor apparatus supports long-term 3-D tissue development because it ensures the nutrient delivery to and waste removal from the neotissue grown at high cell density in the 3-D matrix. We have successfully grown trophoblast cells in the 3-D perfusion bioreactor apparatus for up to one month with periodic medium changes and sampling. Collateral techniques facilitating reactor assembly and sterilization, control, and sampling are known in the art.

Figure 2:
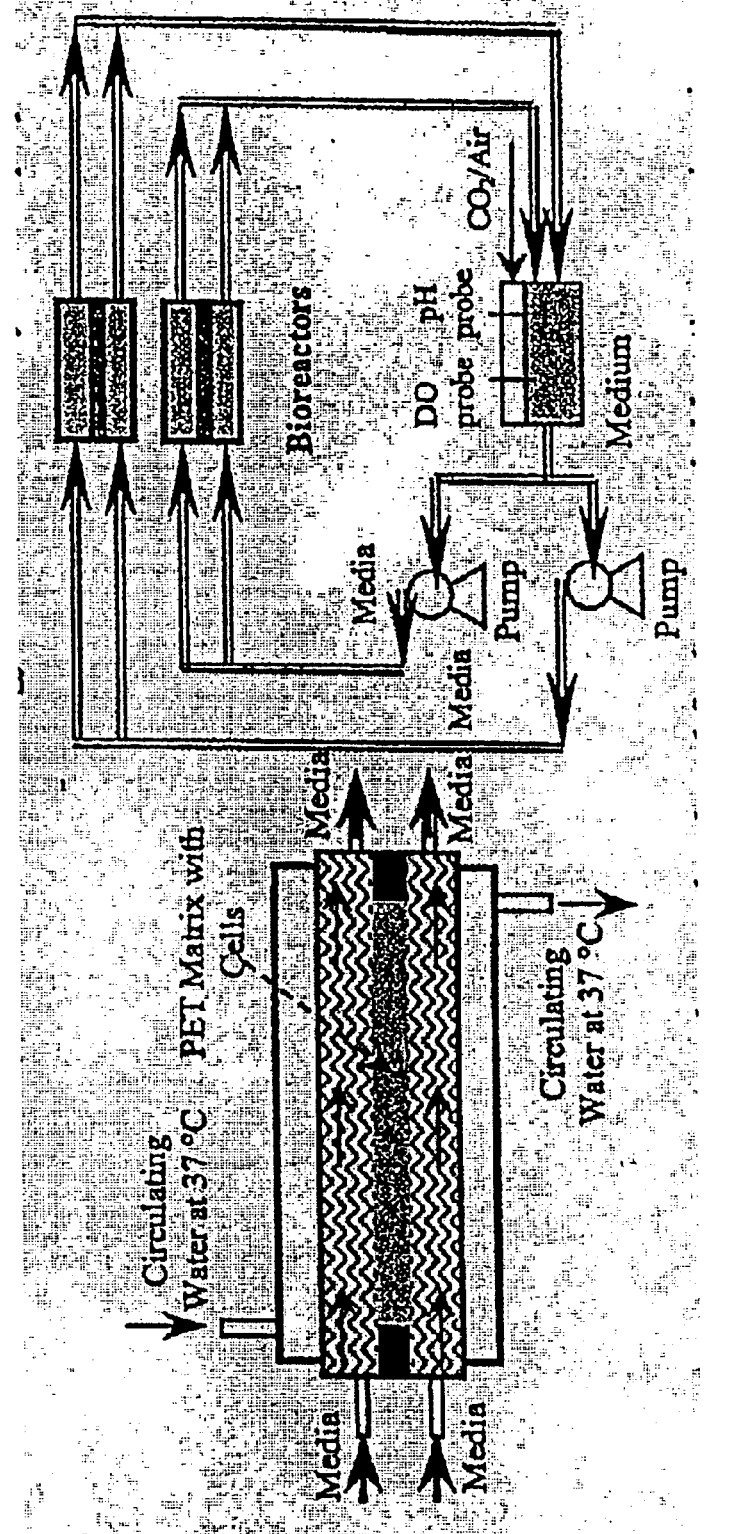
FIG. 2 illustrates a bioreactor apparatus according to an embodiment of the present invention.
Figure 3:
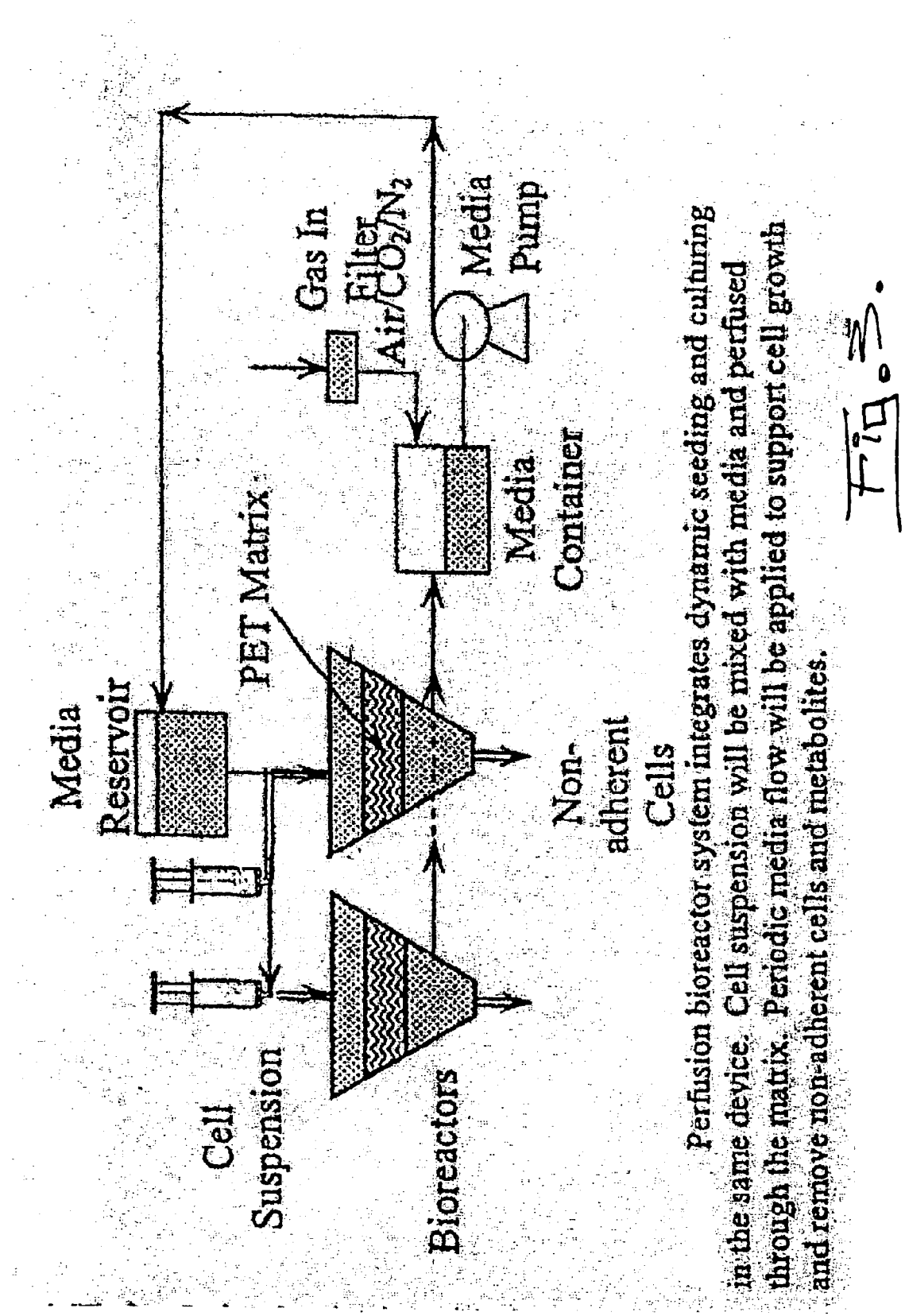
FIG. 3 also shows another embodiment of a bioreactor apparatus according to an embodiment of the present invention.

FIG. 2 shows an embodiment of the present bioreactor apparatus for human tissue engineering. A nonwoven PET matrix with cells was placed in a glass cyclinder and perfused by medium. (B). Two bioreactor chambers were connected in parallel to provide multiple data points. Another embodiment of the present bioreactor apparatus is shown in FIG. 3, including a medium container, a medium reservoir, and a medium-circulating pump. The PET matrix is preferably fixed in a Teflon ring having, for example, a diameter of 3 cm, and a thickness of 1.0 mm, and placed in the middle of a cone-shaped glass vessel. The cone shaped vessel used herein has a bottom diameter of 2 cm, a top diameter of 4 cm, and a height of 6 cm. A reservoir holds the medium and gravitational force will cause the medium to flow through and perfuse the matrix. Non-adherent cells settle at the bottom of the bioreactor vessel and are collected. Spent medium will be transported to a medium container. A pump may be used to transfer medium from the medium container to the medium reservoir. In the medium reservoir, filter-sterilized air and CO2 gas will flow through the reservoir to provide O2 and to control pH in the range of 7.0 to 7.4. A magnetic stirrer and stirring bar may be employed to agitate the medium and to ensure a sufficient oxygenation.

Both of these embodiments integrate dynamic seeding and culturing of cells in the same device. It is important to note that the bioreactor apparatus of the present invention includes two or more cell culture chambers connected in parallel, so that each individual chamber may be disconnected from the bioreactor apparatus as necessary, while the bioreactor continues to operate with its remaining chambers.

Figure 4:
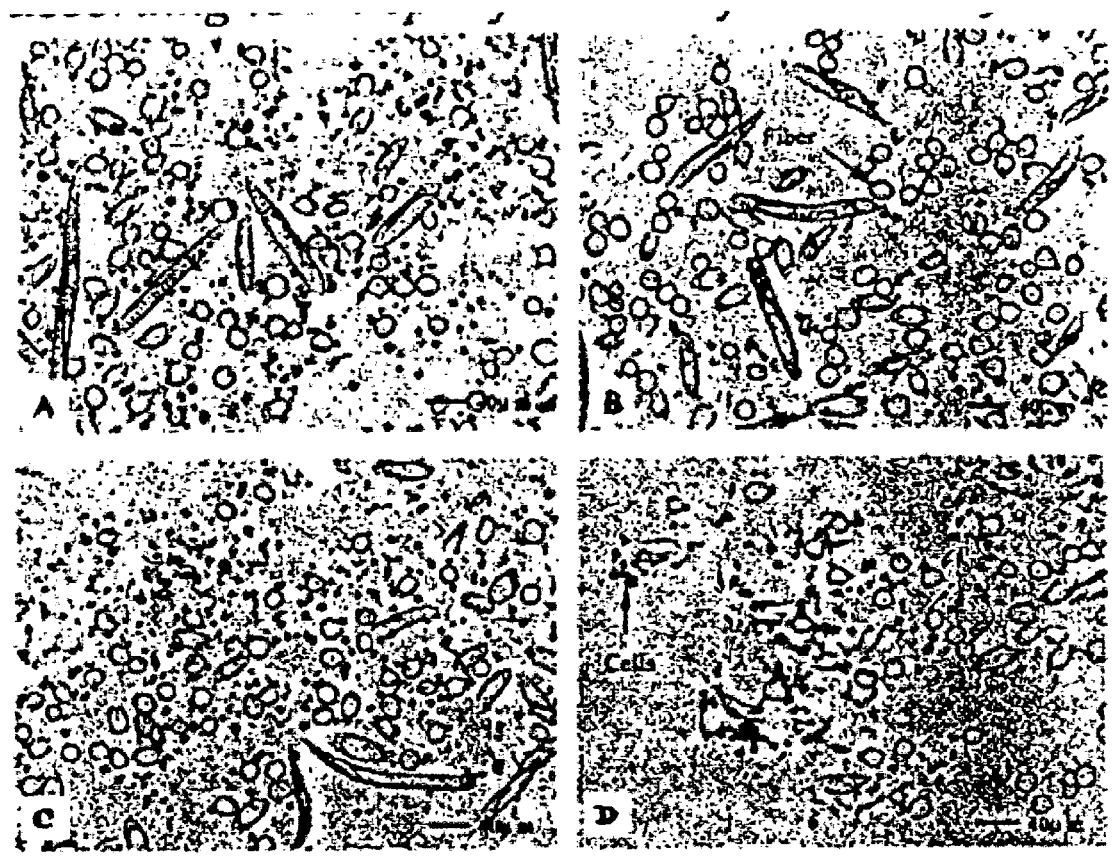
FIG. 4 shows a comparison of cell growth on a three-dimensional matrix following cell seeding by static and dynamic methods.

The present bioreactor apparatus, a perfusion device, may be fabricated based on previously known bioreactors but with some improvements, for example, as shown in FIG. 4. The PET matrix may be sandwiched between two surgical stainless steel plates (W=2.0 cm; L=8 cm) and placed it in the middle of a class cylinder (D=2.3 cm and L=8.5 cm). The matrix will separate the glass cylinder into two compartments with approximately equal volumes. A reservoir holds a cell support medium, and gravitational force may drive the medium flow through the cylinder and perfuse the matrix; alternatively, a pump may be employed for generating a flow of medium. Spent medium will be collected in a cell-liquid separator and non-adherent cells will also be collected. A pump may then transfer medium from the cell-liquid separator to the medium reservoir. In the medium reservoir, filter-sterilized air and CO2 gas preferably flow through the reservoir to provide oxygen and to control pH in the range of 7.0 to 7.4. A magnetic stirrer may be employed to agitate the medium and to ensure a sufficient oxygenation.

Preferred nonwoven PET matrices are used as the 3-D cell culture scaffold, and have the physical parameters of the matrices shown in Table 1. The PET matrices are washed with a scouring solution (1% Na2CO3, 1% v/v Tween.20) and are then treated by boiling in a 1% NaOH solution for one hour. This hydrolysis step reduces surface hydrophobicity, creating carboxyl and hydroxyl groups on fiber surfaces to enhance cell adhesion. The treated matrices are then compressed at approximately 4.5 psi at 121° C. for about 90 min to permanently reduce them to a desired thickness and to reduce the porosity and pore sizes. The compressed matrices are then cut into small portions of approximately 2.0 cm wide by 8.0 cm long, and sandwiched between two surgical stainless steel plates. The skilled will readily understand that these dimensions are provided as one example of preferred embodiments of the invention but may be varied to suit the specific application. Before being used for cell culture, the materials are washed extensively with tap water, deionized water and ultra-purified deionized water. Prior to addition of medium, the bioreactor apparatus is assembled and sterilized by appropriate autoclaving.

Given the number of cells available from cord blood (CB) units, the cell number available for expansion may be as low as $75 \times 10^6$ cells, and as high as $600 \times 10^6$. We have examined inoculation densities ranging from 0.5 to $4 \times 10^5$ cells per $cm^2$ in two-dimensional systems. Optimal cell expansion was observed at concentrations between 2 and $4 \times 10^5$ cells per $cm^2$ in a 6-well plate without 3-D matrices. Based on its physical parameters, the addition of a 3-D matrix increases the available surface area by approximately 20-fold. The total matrix volume is about 1.5 $cm^3$ and the corresponding surface area is about 450 $cm^2$, so that inoculation densities in the range of $2.0–4.0 \times 10^5$ cells/$cm^2$ were used in this study.

TABLE I

Physical parameters of 3-D nonwoven matrices

| Property | 3-D matrix | Property | 3-D matrix |
|---|---|---|---|
| Fiber diameter | 20 pm | Porosity | 0.849 ± 0.004 |
| Fiber density | 1.35 g/cm$^3$ | Pore size range | 10_60 lm |
| Specific surface area | 278 ± 8 cm/cm$^2$ | Average pore diameter | 30 gm |

Dynamic Cell Seeding and Harvesting in the Bioreactor Apparatus.

Cell seeding is the first step of operation and plays an important role in dictating initial seeded cell number, initial cell spatial distribution, and subsequent cellular processes for cell expansion. Efficient cell seeding will greatly reduce the time required for system operation and an even cell distribution in the matrix will greatly enhance the use of the 3-D matrix and improve the growth conditions. High seeding numbers can improve cell growth, and lower numbers often lead to a lower cell proliferation rate.

The present invention provides a dynamic seeding process to improve cellularity and cell distribution in the 3-D fibrous matrices. First, the wettability of the fibrous matrix is improved by hydrolyzation, as noted above. Additionally, hydrolyzation, matrix porosity, and precoating with serum-containing medium are used to improve medium penetration into the matrix.

In static seeding, a cord blood cell suspension may be used as the seeding inoculum. The inoculum is added by injecting the cell suspension into the medium, wherefrom cells will gradually settle onto the matrix by gravity. Dynamic seeding, however, employs a flow of medium to carry the suspended cells into the matrix, conditions for dynamic seeding being determined for each bioreactor apparatus by changing the concentration of cell suspension, medium flow rate, and duration of the injection. Initially, a concentration of cells in suspension is used in approximately the range of $1.0 \times 10^5$–$5.0 \times 10^6$ cells/ml. The desired seeding concentration is then determined based on achieved seeding efficiency and cell expansion.

From previous studies, FIG. 4 shows that dynamic depth filtration seeding produces a high density and fairly uniform cell distribution pattern in both the central region (A) and near the perimeter (C) of the matrix. Static seeding, on the other hand, produced a non-uniform cell distribution with a low cell density in the central region (B), but more cells in the perimeter area of the matrix (D).

In harvesting the expanded cell population from the bioreactor, concern for maintaining cell surface markers has led to the use of a cell dissociation solution (CDS), which is an EDTA based non-enzymatic technique for harvesting cultures. Unlike cells grown on a 2-D plastic surface, the use of such a cell harvesting reagent alone may not be sufficient to remove cells from the 3-D PET matrix. It is important to adjust harvesting techniques to improve cell recovery. This has been explored by comparing results from experiments using 0.05% trypsin and EDTA side-by-side. After culturing, non-adherent cells are collected by perfusing the matrix with phosphate buffered saline (PBS). This non-adherent fraction is counted separately from the adherent fraction. Adherent cells are harvested either by incubating the matrices for 7 minutes at 37° C. with 0.05% trypsin, or by incubating matrices with CDS (Sigma). The removed adherent cells are then collected and rinsed once more with medium. These techniques reproducibly results high viable cell recovery. Any cells remaining in the matrix after non-adherent and adherent cell removal are visualized by staining and examined using either confocal microscopy, or paraffin embedded sections. Whether harvesting under flow conditions will enhance cell recovery from the 3-D matrix was investigated by perfusing the bioreactor with cell harvesting reagents under flow rates ranging from 0.5–3.0 ml/min. Efficiency of cell harvesting by perfusion was evaluated as noted above for the other techniques.

HSC/HPC Ex Vivo Expansion in 3-D Perfusion Bioreactor Apparatus.

Cord blood mononuclear cells were purchased from Clonetics, Walkersville, Md. The bioreactor apparatus is assembled and operated without cells for about ten to twelve hours, although the exact timing may be varied according to need. The bioreactor is then seeded according to the methods described above. Significant benefits in hematopoietic cell output are detectable after 21 days of culture. In a clinical setting, however, longer culture periods may not be suitable waiting periods for patients. Thus, we have examined culture output at days 6, 12, 18 and 24. Human long term culture medium MyeloCult® H5100 (StemCell Technologies Inc., Vancouver, Canada) is used supplemented with serum. Approximately 300 ml of medium is employed for an initial culture period. After three days, about 100 mL of medium is exchanged with new medium and the spent medium is monitored for glucose and lactate concentrations. At days 6, 12, 18, 24, the cells grown in the matrix are sacrificed to determine cell number and cell morphology. The matrices are washed twice with PBS and those cells dislodged will be considered non-adherent cells. The cell-containing matrix is cut into two pieces having approximately equal area. Cell dissociation solution (CDS, Sigma-Aldrich Co.) is then used to harvest adherent cells from the matrix and to minimize alteration of cell surface characteristics. The cellular samples are then evaluated by scanning electronic microscopy (SEM), hematoxylin and eosin (H&E) staining, and immunocytochemistry analysis using confocal laser microscopy (CLSM), flow cytometry, and colony-forming unit assay. Non-adherent and adherent cells will be mixed together for cell counting and assay of colony-forming units. Results from these assays will provide the kinetics of long-term CB expansion (cell counting and CFU assay), metabolic activities (lactate and glucose), cell morphology (Wright's stain and SEM), cell population distribution (flow cytometry), and organization of different types of cells grown in the matrix (immunocytochemistry staining using CLSM). Quantitative results are expressed as the mean±SD and statistical analysis was carried out using a commercial software package (Minitab® 11 for Windows, Minitab, Inc., State College, Pa.).

Ex Vivo Expansion Of Human Mesenchymal Stromal Cells

The isolation of hMSCs from blood cells was first conducted through adherence to the surface of plastic cultureware followed by non-adherent blood cells being poured off. To date, the strong adherence of hMSC to plastic surfaces remains one of the most effective methods for isolating hMSC from bone marrow cells. This isolation procedure, however, requires multiple washings and it takes several days to obtain a relatively pure hMSC population. Frequent handling of culture is laborious and prone to contamination.

The present invention discloses a depth-filtration method for hMSC seeding onto a 3-D PET matrix. The apparatus operates under periodic flow conditions to remove non-adherent cells and to provide nutrients needed for hMSC expansion. hMSC concentration in suspension and medium perfusion rate are controlled to allow sufficient contact time between hMSC and the PET matrices. A hydrolyzed PET surface has similar properties as plastic cultureware and facilitates hMSC adherence. The perfusion medium flow will not only carry the seed inoculum of hMSC but will also remove nonadherent cells. This depth filtration method is also effective for separating hMSC from human bone marrow mononuclear cells by applying a mixture of hMSC and mononuclear cells to the filtration device. After seeding, the subsequent culture is carried out in the same device without the need for handling the seeded matrix.

Cell Seeding by Depth Filtration.

Human mesenchymal stem cells (hMSC) were obtained from normal human bone marrow and hMSC growth medium was purchased from Clonetics, Inc. (Walkersville, Md.). The hMSC were expanded in a T-flask following the standard method provided by Clonetics, Inc. Briefly, cryovials containing hMSC are removed from liquid nitrogen storage and are thawed. The thawed hMSC are inoculated at a density of $5 \times 10^3$ cm$^2$ and incubated in a $CO_2$ incubator for three days before changing the medium. When the confluence of hMSC is about 80%, the cells are passed to four new T-flasks with approximately the same seeding density. After two passages, the cells are trypsinized and a cell suspension is prepared for seeding onto the PET matrix using the depth filtration method.

Nonwoven PET fibrous matrices are hydrolyzed using a 1 N NaOH solution and then cut into round shape patches with diameter of 3 cm and thickness in the range of 0.5 to 2.0 mm. Patches will be washed thoroughly with de-ionized water, autoclaved, and stacked up to three contiguous layers in the bioreactor. PET matrices having different porosities as shown in Table 2 were used. In previous studies, it has been shown that that the porosity of the matrix has a significant effect on cell seeding and growth.

| Property | diameter (cm) | thickness (mm) | volume (cm$^3$) | porosity | Ave. pore diam (FAm) | Specific Surface Area (cm$^2$/cm$^3$) | Pore size range (flon) |
|---|---|---|---|---|---|---|---|
| LP | 3.00 | 1.00 | 0.7065 | 0.849 | 30 | 278 | 10–60 |
| HP | 3.00 | 1.00 | 0.7065 | 0.895 | 40 | 193 | 25–75 |
| UP | 3.00 | 1.00 | 0.7065 | 0.926 | 75 | 136 | 60–130 |

Table 2. Both LP (low porosity) and HP (high porosity) were prepared by thermally compressing low-porosity and high-porosity matrices, respectively. UP (unpressed) is the unpressed low-porosity matrix. These matrices had the same chemical properties but different porosities and pore size distributions.

Before seeding, medium is introduced into the bioreactor apparatus and is the matrix is incubated overnight, or approximately ten to twelve hours. A 20 ml aliquot of a cell suspension at a concentration of $5 \times 10^5$ cells/ml serves as seeding inoculum. A sterile syringe is used to inject and mix the cell suspension with the medium flow from the reservoir. A source of vacuum, possibly a second sterile syringe, is used to create negative pressure in the medium container. The flow rate of the cell-containing medium, the inoculum, passing through the PET matrix will be controlled at approximately 1 ml/min by adjusting the pressure difference. The cell concentration of the medium is controlled by adjusting the rate of injection of the concentrated cell suspension into the flow of medium. When hMSCs were expanded in T-flasks, a cell seeding density of $5 \times 10^3$ cells/cm$^2$ was recommended. For seeding, however, it is desirable to control the inoculation density in the range of $1 \times 10^3$ to $5 \times 10^4$ cells/cm$^2$ based on known specific surface area and volume of the PET patches (Table 2). The number of cells in the filtration effluent is counted to determine the efficiency of cell retention. Cells retained in the matrix are perfused using fresh medium for 30 minutes every 3 hours to remove non-adherent cells and to provide fresh medium for adherent cells. The system was operated for two days in this manner and the cells were counted in the medium washed out to determine if all the cells are firmly adhered to the surfaces of the matrix. The matrices were then removed from the bioreactor to determine cell morphology and cell organization therein. Cell number was determined using a DNA assay. Cells grown in the matrix were fixed and a scanning electron microscope (SEM) was employed to determine general cell morphology. The matrix with cells was also fixed with 70% ethanol and embedded in paraffin for histologic analysis.

HMSC Isolation from Bone Marrow.

The efficiency of depth filtration method to isolate hMSC directly from human bone marrow was tested. In a simulation, human bone marrow mononuclear cells were mixed with hMSCs in different. The same seeding procedure as described above was followed and non-adherent cells were collected when washed out by perfusion medium flow. Non-adherent cells were counted to determine the retention efficiency. After twenty four hours, the matrix was removed and a determination was made of the epitope profile of the adherent cells using the methods previously described.

Effects of Seeding Conditions and Matrix Porosity on hMSC Expansion.

In two-dimensional culture, it is known that hMSC tend to exhibit higher growth rates when plated under very low density, thus indicating that a large surface area is required to obtain a large quantity of cells. In addition, a gradually increasing loss in the doubling potential of the cell population after a first passage has been observed, suggesting that the multiple passages required in conventional culture in plastic cultureware may exert adverse effects on hMSC's expansion and multi-lineage potentials.

More importantly, successful closure of large wounds such as bone defects requires a large cellular replacement with desired functions. Thus, cultivation of hMSC in 3-D matrix is not only a novel approach for ex vivo hMSC expansion but also an effective means to produce functional tissue for transplantation. A nonwoven fibrous matrix has high specific surface area and is uniquely adapted to serve as a scaffold for hMSC expansion. In addition, it is possible to control the pore diameter of a non-woven PET matrix, ranging from 10–150 μm.

hMSCs were seeded into the bioreactor using the depth filtration method described above. The oxygen tension of the medium in the medium container was controlled at about 20% at a pH of 7.2 by adjusting the ratio of air to CO2. The periodic medium flow was induced for a half hour every 3 hours at about 1 ml/min. This periodic medium flow will not only deliver nutrients and remove the metabolites but will also remove non-adherent cells. Two bioreactor cell culture chambers were connected in the apparatus in parallel so that one may be removed for sampling without interrupting the operation of the entire apparatus.

Cell Number and Cell Cycle Analysis.

A DNA assay was used to determine total cell number for the cells grown in the matrix. After inoculation using the depth filtration method, the cells were cultured in the matrix for up to 30 days. Samples of matrices were taken using sterile technique at days 3, 5, 8, 12, 15, 30 and analyzed for DNA contents to determine cell number. Six matrices were employed for each data point. MSC cell cycle analysis was conducted by measuring DNA content by flow cytometry.

Human MSCs grown in the matrices with different inoculation densities were trypsinized, permeabilized with 70% ethanol (10 min at 4° C.), and labeled with 10 mg/ml PI (Sigma), followed by treatment with 0.1 mg/ml RNAse A. A FACScan flow cytometer is used to analyze DNA content and distribution in different cell cycle stages. This assay was performed at days 3, 8, 15, and 30, the results from this assay, cell proliferation kinetics, and cell spatial growth pattern providing detailed information on how different seeding conditions, matrix porosity, and cell organization affect hMSC growth.

Morphology and Histological Analysis.

Scanning electron microscopy (SEM) was used to examine the morphology of the cells grown in the matrices at days 5, 12, and 30. The specimens were fixed with 1.6% glutaraldehyde in 0.1 mole/L cacodylate buffer for 24 hr immediumtely after removal of PBS solution and dehydrated in graded ethanol solution, followed by drying in a critical point dryer. After sputter coating with gold/palladium, the samples were examined in a JEOL JSM 840 SEM. The cells grown in the matrices were also fixed, embedded in paraffin, and observed in cross sections after H&E staining. Histological studies aid in determining cell distribution in the matrix.

Spatial Growth Pattern.

Spatial growth pattern of the cultured cells was determined by the distribution of cells at different cell cycle stages. This is important in elucidating the relationship between the cell cycle stage and its local environment. Immunocytochemical staining and confocal microscopy were employed to obtain images of the distribution of specific cell cycle markers. At days 3, 8, 15, and 30, the cell-containing matrices were incubated with 5-bromo-deoxyuridine (BrdU) containing medium (0.5 mM) for 4 hrs. As known by the skilled, BrdU is a thymidine analogue that can only be incorporated into the proliferating cells undergoing DNA synthesis (cells in S phase). Cells containing BrdU were then detected by a published immunocytochemistry method (Ma T, Li Y, Yang ST, Kniss DA Tissue engineering human placenta trophoblast cells in 3-D fibrous matrix: spatial effects on cell proliferation and function. Biotechnology Progress. Biotechnol Prog 1999; 15:715–24; and Ma T, Li Y, Yang ST, Kniss DA Effects of trophoblast cell organization in fibrous matrix on long-term tissue development and cell cycle. Biotech Biotechnol 2000; 70:606–18).

To determine the fractions of proliferating cells in the matrix, the entire cell-containing matrix was also counterstained by propidium iodide (PI) after incubation with FITC-conjugated secondary antibody. PI is a nucleic acid dye that would stain all the cell nuclei regardless of the cell cycle stage (Id.). The cell images of the same sample obtained at these two different wavelengths allow one to identify proliferating and nonproliferating cells in the matrix. Negative controls were prepared for cultures grown without BrdU, following the same fixation procedures and stained with the secondary antibody only. Negative controls were also be prepared for cells only stained by PI, following the same fixation procedures. Also detected were the expression of $p21^{o}1P"$, p27k1PI, cyclin B and cyclin D and determine the spatial SMC growth patterns following the above method without pre-incubation with BrdU. Propidium iodide counterstaining was performed when necessary.

Figure 5:
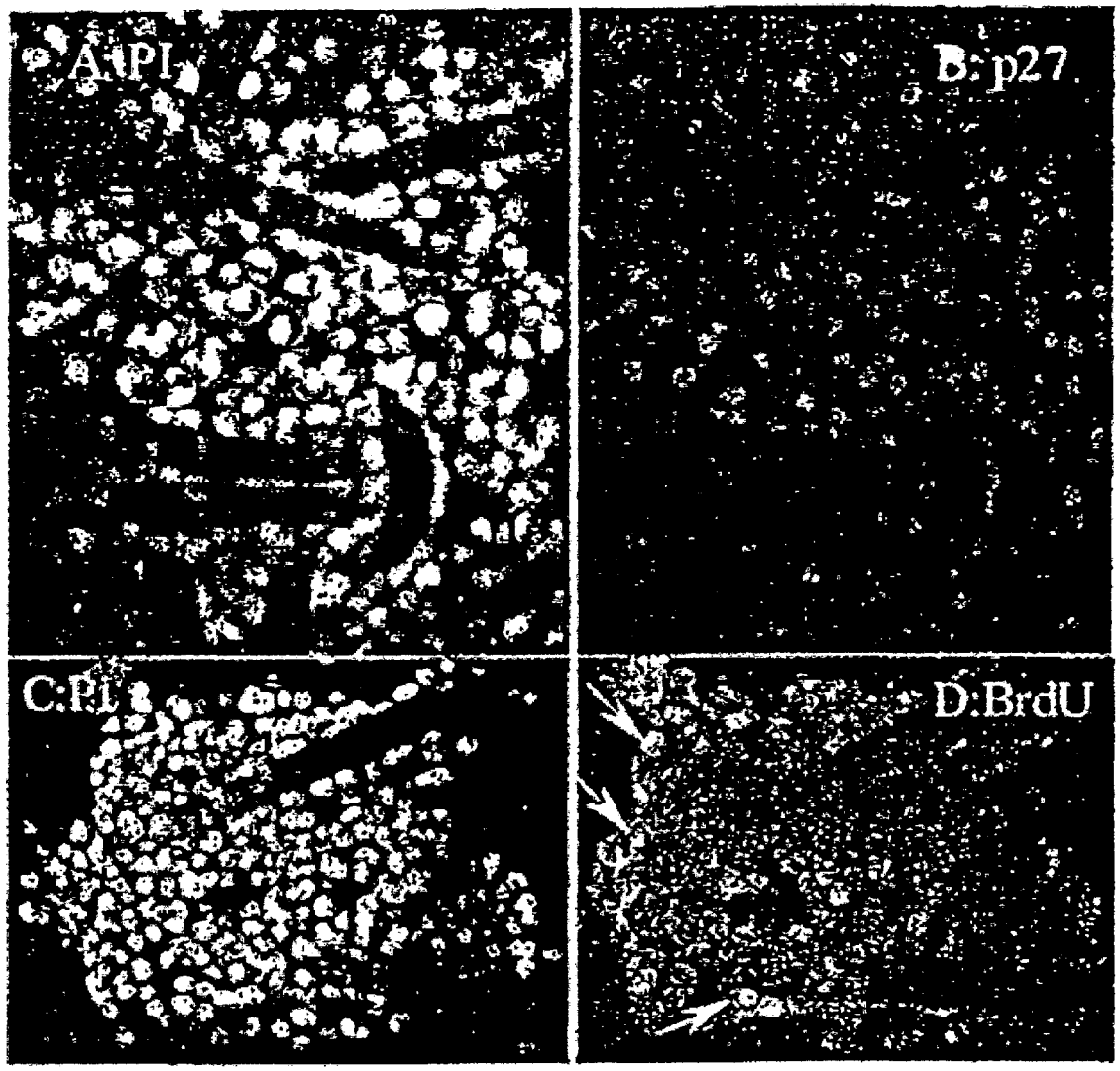
FIG. 5 shows (A) PI staining of the 6th slice of a total 10 slices; (B) p27-FITC staining of the same image; (C) PI staining of the 6th slice of a total of 9 slices; and (D) BrdU-FITC staining of the same image.

FIG. 5 shows (A) PI staining of the 6th slice of a total 10 slices; (B) p27-FITC staining of the same image; (C) PI staining of the 6th slice of a total of 9 slices; and (D) BrdU-FITC staining of the same image. Note that most of the cells in the center of the aggregates are p27 positive, whereas BrdU incorporated cells are at the rim of the aggregate.

Epitope Profile.

The expression of specific cell surface markers for phenotypic characterization of MSC was also detected. Cells were detached with 0.07% EDTA, washed with PBS containing 2% FBS, and incubated with specific antibody at the concentration 1:100 to 1:1000, determined by titration. After incubation, cells were washed with blocking buffer and incubated with secondary antibody (FITC-conjugated mouse IgG). The antibodies used included CD34, CD45, CK18, CK19, VCAM-1, vWF, SH2, SH3, and SH4. CD34 and CD45 are hematopoietic cell markers and hMSCs are CD34 and CD45 negative. Previous studies have found that hMSC are positive for CK18, CK19, VCAM-1, vWF, SH2, SH3, and SH4 and these antibodies were used to determine the expressions of these markers by hMSC grown in the matrices on days 3, 8, 15, and 30.

Alkaline Phosphata e and Calcium Assay.

Detection of alkaline phosphatase activity on days 8, 15, and 30 was carried out. Briefly, triplicate cultures from each experiment were collected and 1 ml, of a 1 mg/ml solution of alkaline phosphatase substrate (p-nitrophenyl phosphate) in a buffer containing 50 mM glycine and 1 mM $MgCl_2 \cdot 6H2O$ will be added. After 10 minutes the solution is removed and mixed with 1 M NaOH solution. The solution is diluted, transferred to a 96-well plate and read at 405 nm using a microplate reader (Bio-Rad Laboratories, Hercules, Calif.). Calcium assay was performed on day 8, 15, and 30.

Cells grown in the matrices were rinsed with Tyrode salt buffer solution and fixed with 1% (v/v) glutaraldehyde in Tyrode's for 30 min. Samples are then rinsed with dionized water and allowed to dry. Calcium is extracted with 3 ml of 0.6 M HCl by immersing the matrix in the solution overnight while rocking. Periodic pipetting was applied when necessary. Aliquots were diluted and a commercial calcium assay kit was employed with the samples. The absorbance was read at 575 nm with a microplate reader (Bio-Rad Laboratories, Hercules, Calif.). The total amount of alkaline phosphatase and calcium was normalized by DNA content determined by DNA assay.

Effects of Oxygen Tension on hMSC Expansion in the Apparatus.

In vivo, oxygen tension of bone marrow is in the 27–49 mmHg range, corresponding to an $O_2$ concentration of approximately 4–7%. This value is significantly lower than what is used in standard $CO_2$ incubator where most previous hMSC experiments have been conducted. The perfusion bioreactor apparatus herein described was used to examine hMSC growth and differentiation under 1%, 2%, 5%, 10%, and 20% oxygen tension.

Figure 6:
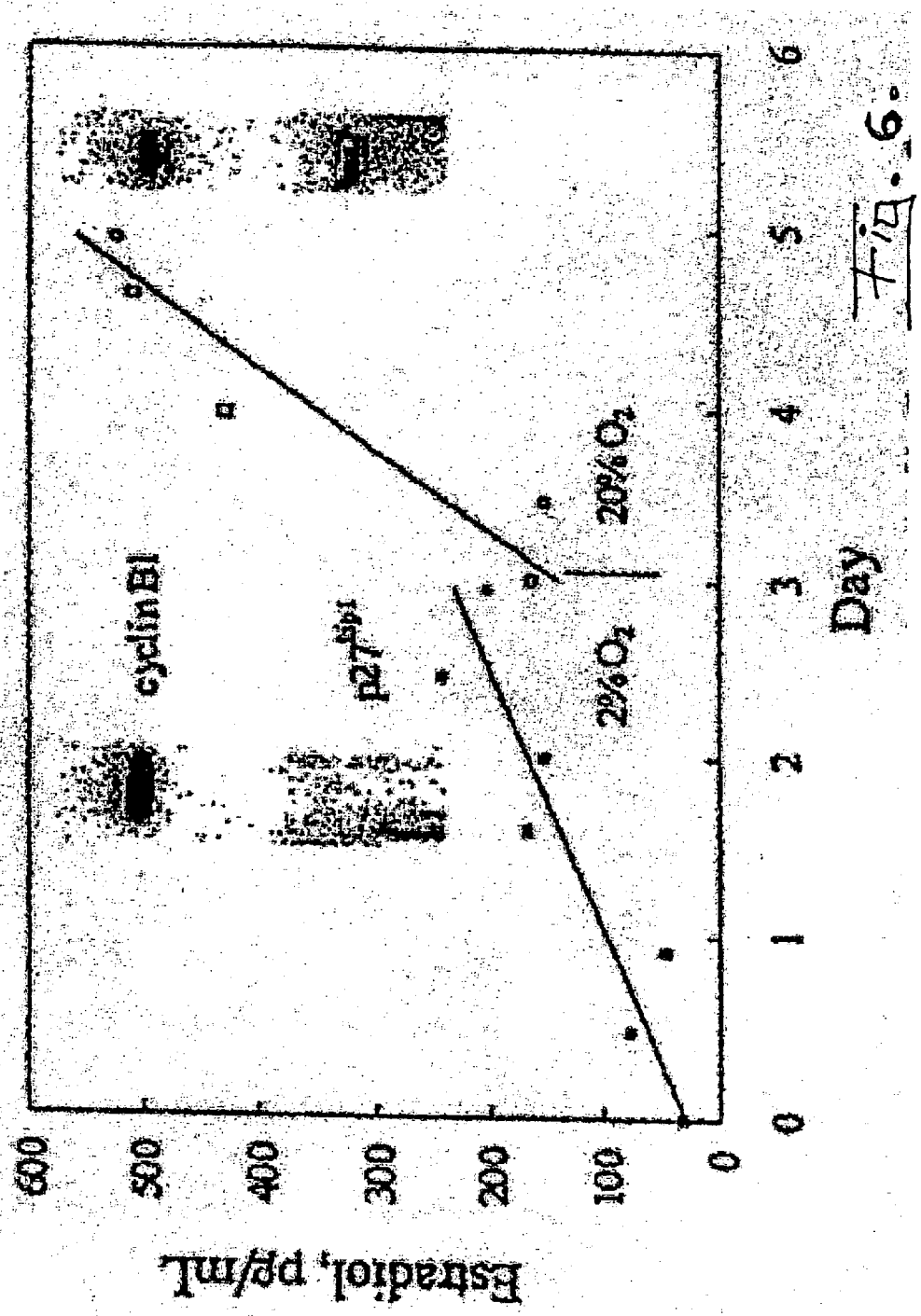
FIG. 6 shows stimulation of high estradiol secretion, p27 expression, and reduced cyclin B1 by human trophoblasts grown in the bioreactor with $O_2$ increased from 2% to 20% at day 3.

The same procedure described above was used to operate the bioreactor apparatus. After seeding, the $O_2$ tension of the medium was controlled by adjusting the ratio of $O_2$ $N_2$, and air circulating in the medium container. The $O_2$ tension is detected by a dissolved oxygen (DO) probe, and controlled at the desired levels of 1%, 2%, 5%, 10%, and 20%. This is achieved by adjusting the flow rates of $CO_2$, $N_2$, and air, which are automatically controlled by the DO controller connected to the air, $N_2$, and $CO_2$ pumps. The cellular and medium samples were collected at different time points to determine hMSC growth and differentiation under different $O_2$ tensions. Assays were conducted following the same procedures outlined above. As an example of the effect of $O_2$ on cell growth and differentiation, FIG. 6 shows stimulation of high estradiol secretion, p27 expression, and reduced cyclin B1 by human trophoblasts grown in the bioreactor with $O_2$ increased from 2% to 20% at day 3.

A DNA assay was used to determine total cell number for the cells grown in the matrix under 1%, 2%, 5%, 10%, and 20% $O_2$. After inoculation using the depth filtration method, cell samples were collected on days 3, 5, 8, 12, 15, 30 and analyzed for DNA contents of the matrices to determine cell number. Three matrices were used for each data point. MSC cell cycle analysis was conducted by measuring DNA content by flow cytometry for each condition. Morphologv and histological analyses were conducted using scanning electron microscopy (SEM) to examine the morphology of the cells grown in the matrices at days 5, 12, and 30 under 1%, 2%, 5%, 10%, and 20% $O_2$.

The same procedure outline above was used to determine spatial growth pattern by examining the distribution of cells grown under 1%, 2%, 5%, 10%, and 20% $O_2$ at different cell cycle stage.

Expression of specific cell surface makers was detected for phenotypic characterization of hMSCs grown under 1%, 2%, 5%, 10%, and 20% $O_2$. Finally, alkaline phosphatase and calcium assays were conducted on days 8, 15, and 30 for hMSCs grown under 1%, 2%, 5%, 10%, and 20% $O_2$.

Example of the Modular Cell Culture Bioreactor in Operation

Figure 7:
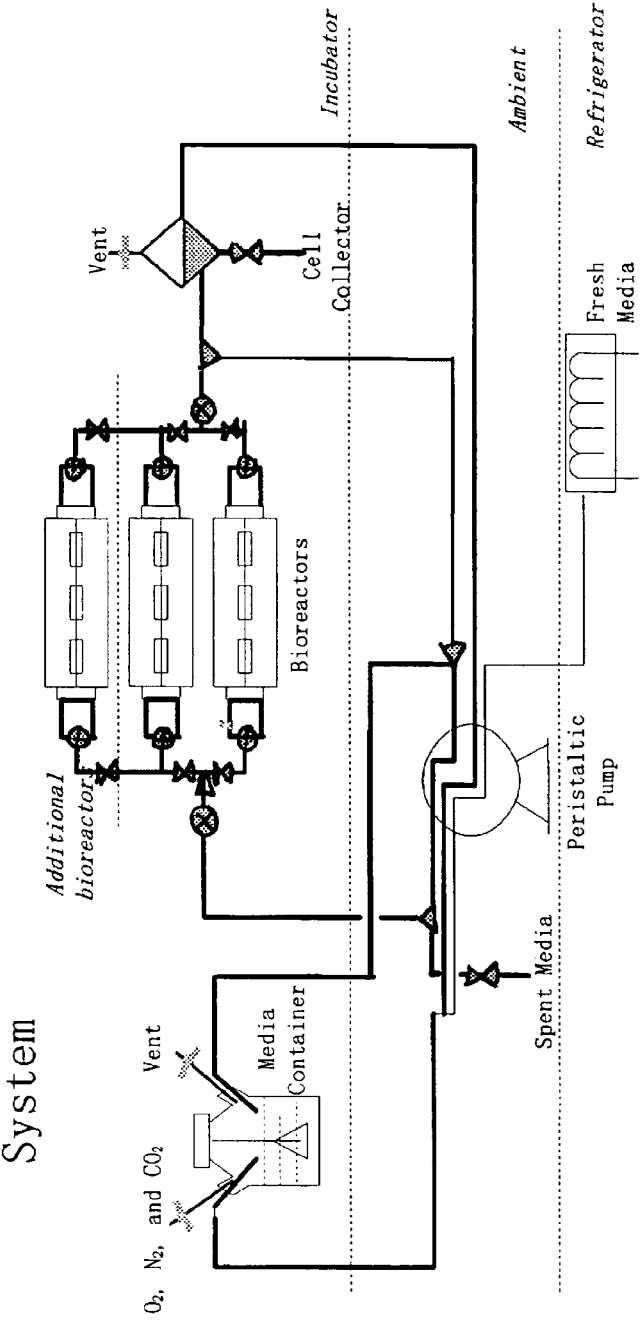
FIG. 7 is a flow diagram of a bioreactor apparatus according to the present invention, showing the valves and ports employed in the apparatus.

FIGS. 7–13 illustrate a typical modular bioreactor apparatus according to the present invention, and various cell activity parameters associated therewith. FIG. 7 shows a flow diagram of a bioreactor apparatus according to the present invention, showing the valves and ports employed in the apparatus. It should be noted that each bioreactor cell culture chamber has three matrices therein. During dynamic seeding by depth filtration, only one inlet port is open, and only one outlet port is open but on an opposite side of the matrices from the open inlet port. This arrangement creates a flow of medium carrying cells from the open inlet port, through the matrices, and out the open outlet port. This dynamic cell seeding cycle may be repeated a number of times in order to allow a high proportion of the cells to adhere to a matrix. FIG. 8, for example, shows a graph illustrating removal of seeded cells by a bioreactor matrix during consecutive passes through the matrix. FIG. 9 is a bar graph showing the distribution of cells seeded into a bioreactor chamber in the apparatus of FIG. 7, wherein each bioreactor has three matrices, as shown. As the medium flow during seeding is essentially parallel through the three matrices, it appears that the matrices retain an approximately equal number of adhering cells regardless of whether the matrix is in position one, two or three in the bioreactor chamber. FIG. 10 shows a bar graph depicting distribution of seeded cells onto matrices 1, 2 and 3 during four consecutive passes of a seed cell inoculum in the apparatus of FIG. 7, indicating the approximately equal distribution of cells.

Cell growth parameters in the apparatus of FIG. 7 are shown in FIGS. 11–13. For example, FIG. 11 is a line graph showing typical oxygen consumption of human mesenchymal stromal cells in a bioreactor at ambient $O_2$ tension. FIG. 12 is a line graph showing glucose and lactate levels at bioreactor chamber inlet and outlet as measures of cell metabolism in the apparatus of FIG. 7. Finally, FIG. 13 shows bioreactor chamber inlet and outlet levels of lactic acid dehydrogenase (LDH) during cell culture in the apparatus of FIG. 6. These indicators point to healthy cell growth during operation of the modular apparatus described herein.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

What is claimed is:

1. A method of seeding and culturing cells, the method comprising:

seeding the cells by generating a flow of medium carrying an inoculum containing cells through a three-dimensional nonwoven fibrous matrix of polyethylene terephthalate so as to filter the medium therethrough at a flow rate effective for permitting adherence of predetermined cells to the matrix;

diverting the flow of medium after filtering so that the diverted medium flows primarily along outer peripheries of the matrix; and culturing the adherent cells by perfusing the diverted flow of medium to contact the outer peripheries of the matrix at a flow rate effective for allowing diffusion of cell nutrients and cell waste products through the matrix.

2. The method of claim 1, further comprising removing non-adherent cells from the medium after seeding.

3. The method of claim 1, wherein the inoculum consists of a sample of human bone marrow.

4. The method of claim 1, wherein the inoculum contains human mesenchymal stromal cells.

5. The method of claim 1, wherein the inoculum contains human hematopoietic stem cells.

6. The method of claim 1, wherein filtering and diverting are carried out within a single cell culture chamber.

7. The method of claim 1, wherein filtering and diverting are carried out substantially simultaneously in a plurality of cell culture chambers.

8. The method of claim 1, wherein filtering and diverting are carried out without handling the matrix.

9. A method of seeding and culturing cells, the method comprising:

seeding the cells by generating a flow of medium carrying an inoculum containing cells through a three-dimensional nonwoven fibrous matrix of polyethylene terephthalate so as to filter the medium therethrough at a flow rate effective for permitting adherence of predetermined cells to the matrix;

monitoring cell count in the filtered medium as an indicator of cell adherence to the matrix and continuing filtration until a predetermined proportion of cells has adhered;

diverting the flow of medium after filtering so that the diverted medium flows primarily along outer peripheries of the matrix; and culturing the adherent cells by perfusing the diverted flow of medium to contact the outer peripheries of the matrix at a flow rate effective for allowing diffusion of cell nutrients and cell waste products through the matrix.

10. The method of claim 9, further comprising removing non-adherent cells from the medium after seeding.

11. The method of claim 9, wherein the inoculum consists of a sample of human bone marrow.

12. The method of claim 9, wherein the inoculum contains human mesenchymal stromal cells.

13. The method of claim 9, wherein the inoculum contains human hematopoietic stem cells.

14. The method of claim 9, wherein filtering and diverting are carried out within a single cell culture chamber.

15. The method of claim 9, wherein filtering and diverting are carried out substantially simultaneously in a plurality of cell culture chambers.

16. The method of claim 9, wherein filtering and diverting are carried out without handling the matrix.

* * * * *